United States Patent [19]
Ulmer et al.

[11] Patent Number: 5,869,695
[45] Date of Patent: Feb. 9, 1999

[54] PROCESS FOR MAKING DERIVATIZED POLYMERS OF MALEIC ANHYDRIDE CONTAINING MALEAMIC ACID AND ITS CORRESPONDING CYCLIC IMIDE REPEAT UNITS

[75] Inventors: Herbert W. Ulmer, Hoboken; John A. Katirgis, Bergenfield, both of N.J.

[73] Assignee: ISP Investments Inc., Wilmington, Del.

[21] Appl. No.: 845,669

[22] Filed: Apr. 25, 1997

[51] Int. Cl.$^6$ .................. C10M 133/16; C07D 207/40
[52] U.S. Cl. .................. 548/545; 548/546; 548/547
[58] Field of Search .................... 548/545, 546, 548/547

[56] References Cited

U.S. PATENT DOCUMENTS

| | | | |
|---|---|---|---|
| 2,262,262 | 11/1941 | Speer | 548/545 X |
| 4,839,072 | 6/1989 | Gutierrez et al. | 548/545 X |
| 4,841,069 | 6/1989 | Olsen | 548/545 |
| 5,554,768 | 9/1996 | Donges et al. | 540/545 |

FOREIGN PATENT DOCUMENTS 0545202  8/1957  Canada .................. 548/545

*Primary Examiner*—Floyd D. Higel
*Attorney, Agent, or Firm*—Walter Katz; Marilyn J. Maue; William J. Davis

[57] ABSTRACT

A process for making derivatized polymers of maleic anhydride containing maleamic acid and its corresponding cyclic imide repeat units, in alcohol solution, at a temperature of about 60°–160° C., during a reaction period of about 1–25 hours. The product is a polymer having a predetermined ratio of the above repeat units.

12 Claims, 3 Drawing Sheets

PROCESS FOR MAKING DERIVATIZED POLYMERS OF MALEIC ANHYDRIDE CONTAINING MALEAMIC ACID AND ITS CORRESPONDING CYCLIC IMIDE REPEAT UNITS

BACKGROUND OF THE INVENTION

1. Field of the Invention

This invention relates to polymers of maleic anhydride, and, more particularly, to a process of making derivatized maleic anhydride polymers which include maleamic acid and/or its cyclic imide repeat units.

2. Description of the Prior Art

Amines can be reacted with maleic anhydride to give the corresponding half-amide derivative. Generally, a polymer containing maleic anhydride is reacted in solution or suspension with an amine in an inert or non-reactive solvent, such as acetone, heptane, benzene or dibutylether, to provide the desired half-amide derivative. This material then must be isolated and repackaged into a useful product.

Unfortunately, various side reactions occur during such solution or suspension processes. These side reactions adversely affect the quality of the final product, particularly its color and odor. The amine reactant also can form a salt with the half-acid polymer instead of reacting with the anhydride and reduce the yield of the desired amide reaction product.

The reaction of amines with anhydride polymers in an inert solvent also is difficult to control because of its rapid reaction rate and high reaction exotherm leading to the formation of a non-homogeneous reaction product.

Reactions of anhydride polymers with amines in inert solvents present other problems, too. For example, if the reaction is conducted as a slurry, e.g. reaction of p(methyl vinyl ether-maleic anhydride copolymer) with an amine in toluene, the consistency of the slurry may change as the amine reacts with the anhydride polymer. This consistency change usually results in excessive swelling of the polymer during the reaction, which can make subsequent processing very difficult unless the slurry is sufficiently diluted with solvent. However dilution reduces polymer capacity. Reaction of the anhydride polymer as a solution in an inert solvent such as acetone with amine is advantageous but it may result in considerable gelling or precipitation of the reaction product or the formation of "fish eyes".

Similar reactions of anhydride polymers with amines in a reactive solvent such as ethanol may solve these problems because the resultant products are generally made available in the form of homogeneous solution or stable colloidal suspensions which are easy to handle even at a high solids content.

Accordingly, it is an object of this invention to provide a new and improved process of making derivatized maleic anhydride polymers, and, particularly, to a process of making substantially homogeneous maleic anhydride-containing polymers which include maleamic acid and its cyclic imide derivatives.

Another object herein is to provide a process of making polymers containing a maleic anhydride, and its maleamic acid and corresponding cyclic imide derivatives, in a predetermined ratio of each.

A feature of the invention is the provision of such process which is carried out in an alcohol as a reactive solvent.

Another feature of the invention is to control the reaction temperature and period of reaction during the process to predetermine the ratio of each of the maleic anhydride-half-ester, maleamic acid and cyclic imide repeat units of the polymer obtained.

Yet another feature herein is to provide a derivatizing reaction which can be carried forward substantially to completion with little or no unwanted side reactions.

Yet another feature is a derivatization reaction which does not need an esterification or acidification catalyst, and is conducted in a non-toxic solvent.

Among the other features of the invention is the provision of a terpolymer product having little color or odor and little free amine.

These and other objects and features of the invention will be made apparent from the following detailed description of the invention.

SUMMARY OF THE INVENTION

What is described herein is a process of forming a polymer which includes the following repeat units:

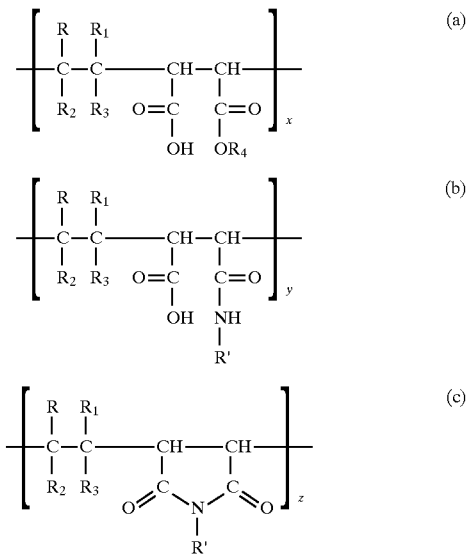

where R, $R_1$, $R_2$ and $R_3$ are selected from H, alkyl, alkoxy, cycloalkyl, aryl, ester, acid, fluoro and silyl and $R_4$ is alkyl; R' is hydrogen, aryl, alkyl or alkyl derivatized with fluoro, silyl, amino or olefinic; and x is 0.05–0.95, y=0–0.9 and z=0.05–0.95; which comprises reacting: in alcohol solution, $R_4OH$, where R, $R_1$, $R_2$ and $R_3$ are as defined above, and $R_4$ is as defined above, with an α-unsubstituted primary amine, $R'NH_2$, where R' is as defined above, at a temperature of about 60°–160° C., for a predetermined period of time.

In the preferred embodiments of the invention, the reaction temperature is about 80°–150° C., most preferably about 100°–120° C., and the reaction time is about 1–25 hours, most preferably about 2–10 hours.

A preferred starting copolymer is an alkyl vinyl ether-maleic anhydride copolymer, such as methyl vinyl ether-maleic anhydride copolymer (MVE-MAn), or its corresponding half-ester, or isobutylene-maleic anhydride copolymer (IB-MAn), or its corresponding half-ester or ethylene-maleic anhydride copolymer (ET-MAn), or its corresponding half-ester or styrene-maleic anhydride copolymer (STy-MAn), or its corresponding half-ester.

The preferred α-unsubstituted amines are $C_1$ to $C_{-40}$ alkyl α-unsubstituted primary amines, such as n-hexylamine, n-octylamine, and 2-ethylhexylamine. Ammonia, silated primary amines, fluorinated primary amines, halogenated primary amines, unsaturated amines, cyano amines and amphoteric amines also may be used.

In one embodiment of the invention, a polymer having no amide component, i.e. all amide has been converted to the cyclic imide form, can be obtained by carrying out the process at 115° C. for 5 hours or longer. The resultant polymer thus includes half-ester and cyclic imide repeat units therein.

IN THE DRAWINGS

FIG. 1 is a plot of unreacted amine vs. reaction time to show the course of the derivation reaction with methyl vinyl ether-maleic anhydride copolymer in ethanol solution at various temperatures.

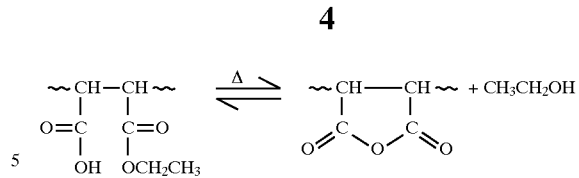

Upon heating this equilibrium reaction mixture to the desired reaction temperature, elimination of alcohol occurs forming the anhydride intermediate. At this point, the added amine reactant can react with the anhydride intermediate to produce the maleamic acid derivative and its cyclic imide. A summary of the reactions involved in the process, and the resultant terpolymer and its repeat units, is shown below:

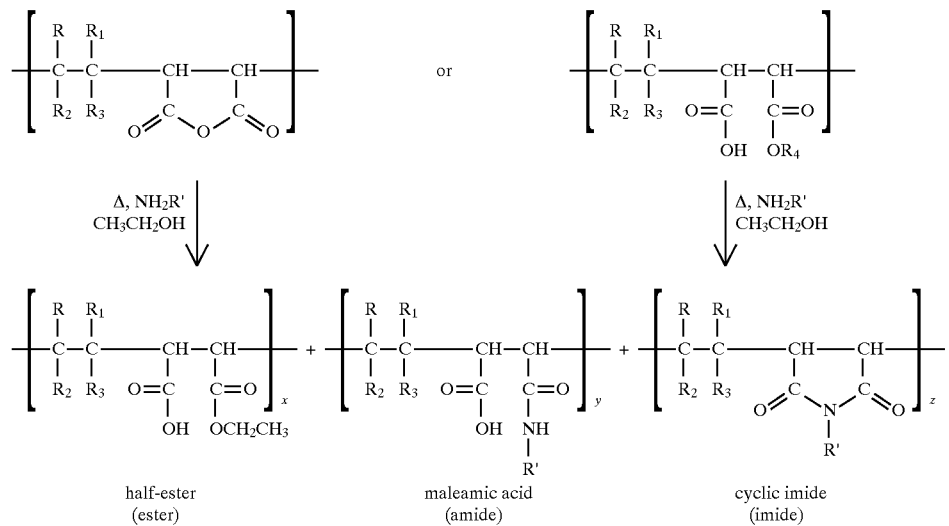

FIG. 2 are plots of mole % of a given repeat unit in the polymer obtained by the process of the invention vs. the period of time of the reaction, at various reaction temperatures.

DETAILED DESCRIPTION OF THE INVENTION

To illustrate this invention, a maleic anhydride (MAn) copolymer in alcohol solution is derivatized with an α-unsubstituted primary amine to form a polymer containing repeat units of the MAn half-ester, its half-amide, and its corresponding cyclic imide. The reaction is carried out at a predetermined temperature and for a predetermined period of time to provide a polymer having a desired ratio of the above repeat units therein.

A suitable starting material for this process is methyl vinyl ether-maleic anhydride (MVE-MAn) copolymer which is commercially available in the form of a powder or solution of the copolymer in acetone solvent. The acetone therein is then removed by solvent-exchange with added ethanol. Then a suitable amine reactant is added to the copolymer-ethanol solution in a predetermined amount to form a reaction mixture containing ethanol as a reactive solvent therein. In the presence of ethanol, the MAn polymer exists therein in equilibrium with its corresponding alkyl half-ester, as shown by the equation below:

Higher reaction temperatures and longer reaction times enhanced the conversion of amide by loss of a water molecule into the corresponding cyclic imide repeating unit.

Figure 1:
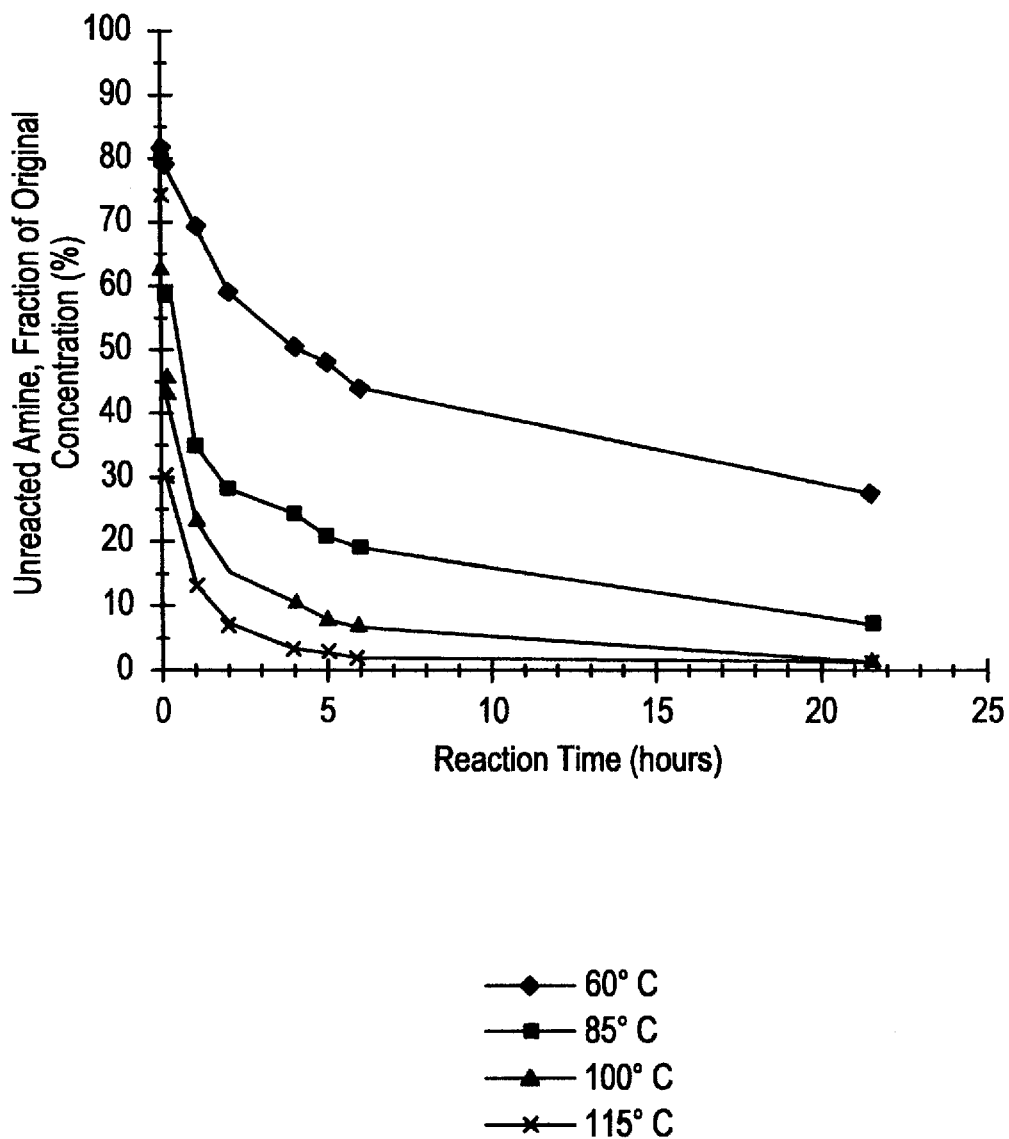
Figure 2A:
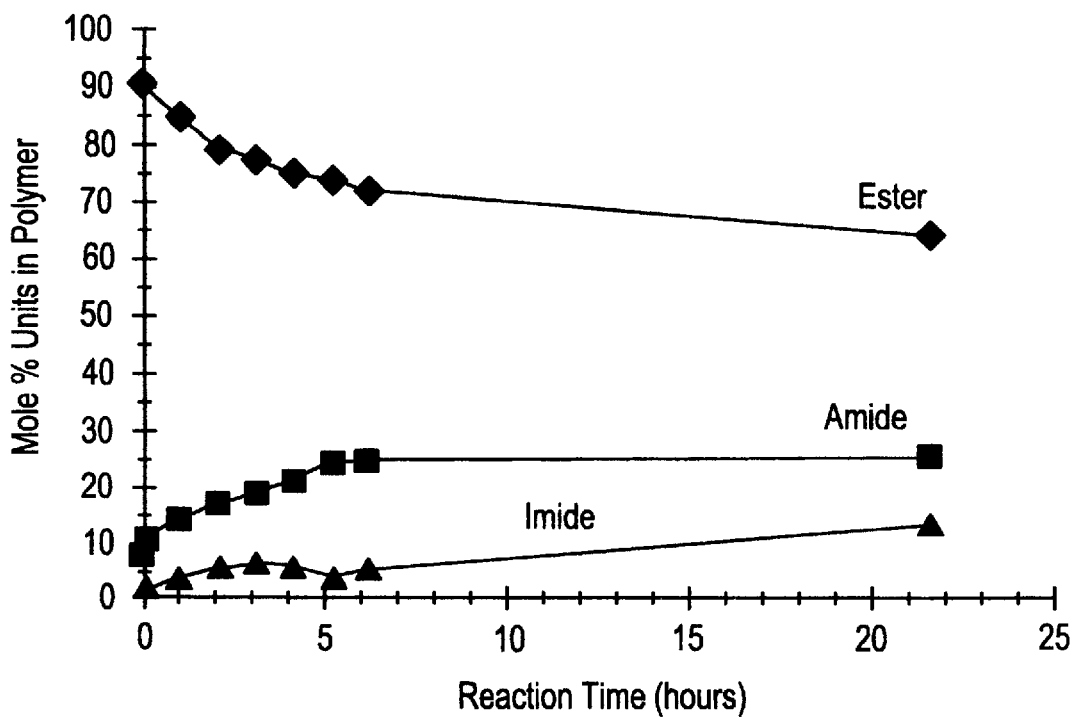
Figure 2B:
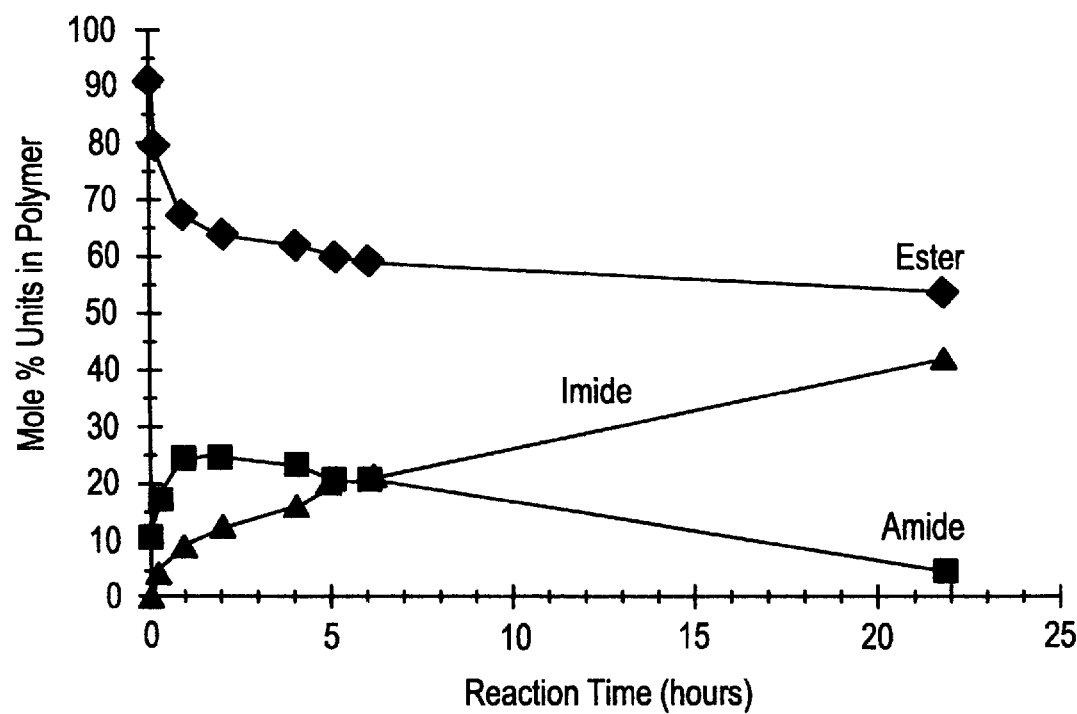
Figure 2C:
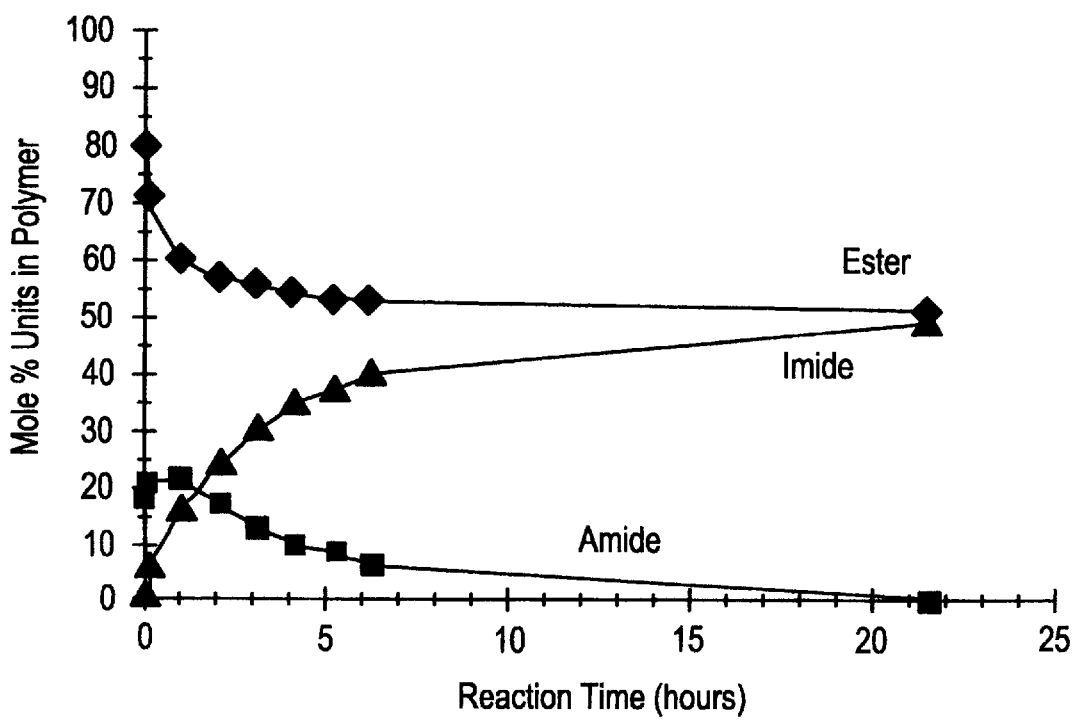
Figure 2D:
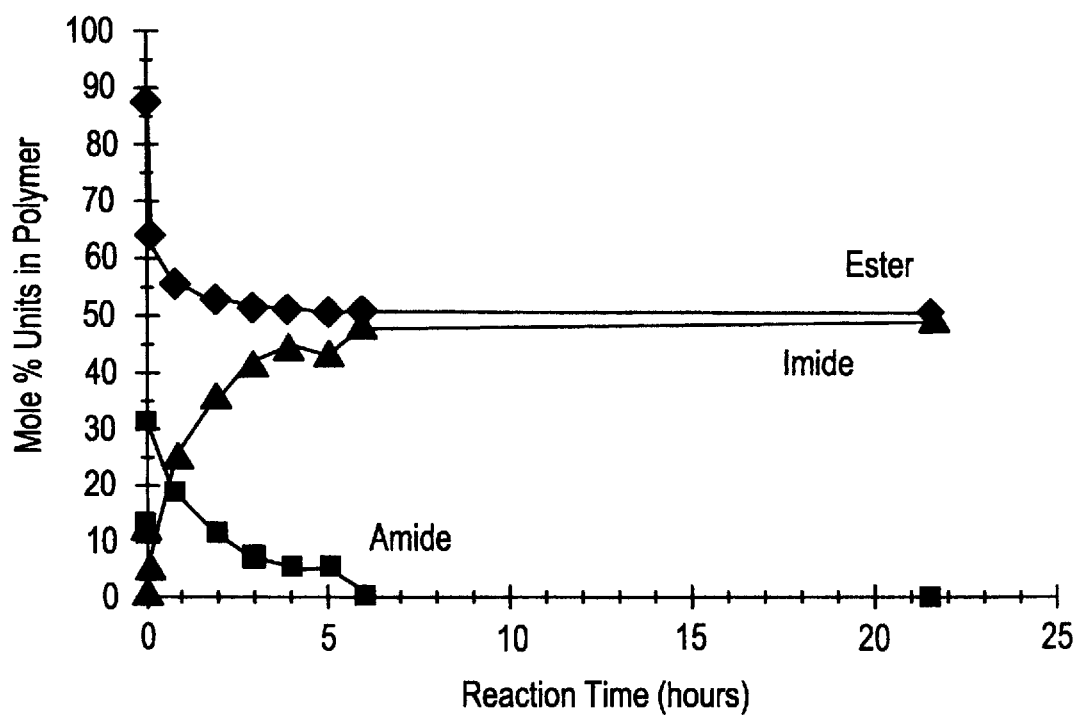

FIG. 1 is a graphical illustration of the course of the reaction of methylvinyl ether-maleic anhydride copolymer and 50 mole % of 2-ethylhexyl amine in ethanol solution at various reaction temperatures, plotted as the percent unreacted amine vs. reaction time. These results show that the reaction is strongly temperature dependent. For example, at 60° C., after over 20 hours, almost 30% of the amine reactant remains, while at 115° C., the reaction is substantially complete after only 5 hours.

EXAMPLE 1

Methyl vinyl ether, MVE, was polymerized with maleic anhydride, MAn, in acetone to give the anhydride copolymer. The material was sparged with ethanol until the level of acetone was below 0.4 wt. percent. The resultant copolymer was the ethyl half-ester of MVE/MAn at approximately 50% solids. The ethanol solution containing polymer was then diluted to approximately 30% solids by the addition of ethanol, and 50 mole % hexylamine reactant was added. The reaction mixture was purged with $N_2$ gas, heated to 85° C. and held for 20 hours. A resultant terpolymer solution was obtained which was yellow-brown in color with an Acid No. of 149 mg KOH/g polymer and less than 2 wt. % free amine.

EXAMPLE 2

As above, the half-ester copolymer in ethanol was diluted with ethanol to give a 30% solids solution. Then 50 mole % n-octylamine was added and the reaction mixture was purged with $N_2$ gas. The reactor was heated to 85° C. and held for approximately 20 hours. The resultant terpolymer solution was brownish in color with an Acid No. of 156 mg KOH/g polymer and less than 3 wt. % free amine present.

EXAMPLE 3

As above, the half-ester copolymer in ethanol was diluted with ethanol to give a 30% solids solution. Then 50 mole % 2-ethylhexylamine was added and the reaction mixture was purged with $N_2$ gas. The reactor was heated to 85° C. and held for 20 hours. The resultant terpolymer solution was brownish in color with an Acid No. of 166 mg KOH/g polymer and less than 2 wt. % free amine present.

EXAMPLE 4

In a high pressure reactor, 30.13 g p(ethylene-MAn) powder was added to 170.30 g ethanol. To the above slurry was added 15.44 g octylamine dissolved in 39.44 g ethanol. Upon such addition, a slight exotherm was observed. The reaction mixture then was purged with $N_2$ gas and the reactor was sealed. The temperature was raised to 100° C. over 2 hours, and held at that temperature for 5 hours, and cooled to room temperature. The product was a clear, yellow solution.

EXAMPLE 5

In a high pressure reactor, 30 g p(ethylene-MAn) powder was added to 200 g ethanol. To the resultant slurry was added:

6.39 g octadecylamine, 9.20 g 2-ethylhexyl amine, and 1.74 g butylamine, dissolved in 40 g ethanol.

After such addition, a slight exotherm was observed. The reactor was purged with $N_2$ gas and the temperature was gradually raised to 100° C. over 2 hours and held at that temperature for an additional 5 hours. Upon cooling, the product obtained was a clear, yellow solution.

EXAMPLE 6

Into a high pressure reactor was added: 75.4 g P(isobutylene-MAn) powder, 19.8 g octadecylamine and 222.1 g ethanol. The reaction mixture was then purged with $N_2$ gas and the temperature was raised to 50° C. and held there for 1 hour. Then the temperature was increased to 75° C., held for 2 hours, and thereafter to 100° C. for 3 hours. Upon cooling the resultant product had a slightly green color and a slight haze. The dried polymer had an acid of 225 mg KOH/g polymer and contained about 2 wt. % free amine.

EXAMPLE 7

In a high pressure reactor was added:

60.86 g p(isobutylene-MAn) powder, 15.90 g n-octadecylamine, 4.32 g n-butylamine, and 270.3 g ethanol.

The resultant reaction slurry was stirred, sealed and purged with $N_2$ gas. The temperature was raised to and kept at 75° C. for 2 hours and then raised to and kept at 100° C. for 5 hours. Upon cooling, the reaction product was a clear slightly yellow solution. The resultant polymer had an Acid No. of 202 mg KOH/g polymer and 0.142 meq. free amine/g of product.

EXAMPLE 8

In a high pressure reactor was added:

65 g p(isobutylene-MAn) powder, 11.4 g octadecylamine, 10.9 g octylamine, and 204 g ethanol.

The resultant slurry was stirred, sealed and purged with $N_2$ gas. The temperature was raised to and kept at 75° C. for 2 hours and then raised to and kept at 100° C. for 5 hours. Upon cooling, the reaction product was a clear slight yellow solution. The resultant polymer had an Acid No. of 198 mg KOH/g polymer and 0.146 meq. free amine/g product.

EXAMPLE 9

The following graphs (FIGS. 1 and 2) show the effect of temperature on the incorporation of α-unsubstituted amines into the MVE/MAn copolymer. The reactions were conducted at varying temperatures with 50 mole % 2-ethylhexylamine as reactant, as described in Example 3. As can be seen from FIG. 1, minimal salt formation is produced at a reaction temperature of 115° C. after only 5 hours of reaction time.* Similar trends were observed with the other α-unsubstituted primary amines of Examples 1 and 8.

* Any unreacted amine results in the formation of salt.

As shown in FIG. 2 below, which represent the polymer composition of P(MVE-MAn) half-ethyl ester copolymers reacted with 50 mole % of 2-ethylhexylamine, the amide-:cyclic imide ratio present in the polymer is largely controlled by the temperature and reaction time conditions. More particularly, an increase in the reaction temperature and an increase in reaction time enhances imide formation over the amide structure in the polymer obtained. In fact, as shown in FIG. 2 at 115° C. and after 5 hours reaction time, the amine reactant, which had been taken up as the amide in the terpolymer, has been converted completely to the cyclic imide form, without requiring removal of water.

The polymers of this invention are particularly useful in personal care and pharmaceutical products.

While the invention has been described with particular reference to certain embodiments thereof, it will be understood that changes and modifications may be made which are within the skill of the art. Accordingly, it is intended to be bound only by the following claims, in which:

What is claimed is:

1. A process of forming a polymer made up of the following repeat units:

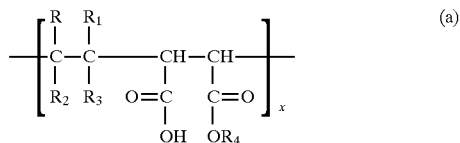

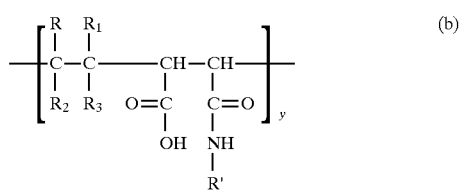

-continued

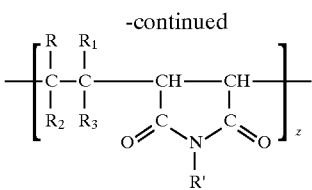
(c)

where R, R₁, R₂ and R₃ are selected from H, alkyl, alkoxy, cycloalkyl, aryl, ester, acid, fluoro and silyl; and R₄ is alkyl; R' is hydrogen, aryl, alkyl or alkyl derivatized with fluoro, silyl, amino or olefinic; and x is 0.05–0.95, y=0–0.9 and z=0.05–0.95; which comprises reacting:

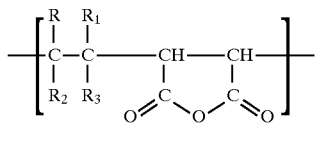
(d)

or

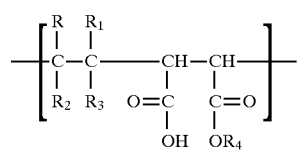
(e)

where R, R₁, R₂ and R₃ are as defined above, in R₄OH alcohol solvent, where R₄ is as defined above, with an α-unsubstituted primary amine, R'NH₂, where R' is as defined above, at a temperature of about 60°–160° C., for a reaction period of about 1–25 hours.

2. A process according to claim 1 wherein the reaction temperature is about 80°–150° C.

3. A process according to claim 1 wherein the reaction temperature is about 100°–120° C.

4. A process according to claim 1 wherein the reaction time is about 2–10 hours.

5. A process according to claim 1 wherein R is alkyl and R₁, R₂ and R₃ are H.

6. A process according to claim 1 wherein R and R₁ are alkyl and R₂ and R₃ are H.

7. A process according to claim 1 wherein R is alkoxy and R₁, R₂ and R₃ are H.

8. A process according to claim 1 wherein

is isobutylene.

9. A process according to claim 1 wherein

is methylvinyl ether.

10. A process according to claim 1 wherein

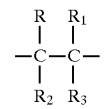

is ethylene.

11. A process according to claim 1 wherein

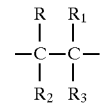

is styrene.

12. The product of the process of claims 1–11.

* * * * *